| United States Patent [19] | [11] Patent Number: 4,927,763 |
| Sudoma et al. | [45] Date of Patent: May 22, 1990 |

[54] STABILIZATION OF DRIED BACTERIA EXTENDED IN PARTICULATE CARRIERS

[75] Inventors: A. Louis Sudoma; Dean G. Dalebroux, both of Milwaukee, Wis.

[73] Assignee: Chr. Hansen's Laboratory, Inc., Milwaukee, Wis.

[21] Appl. No.: 212,515

[22] Filed: Jun. 28, 1988

Related U.S. Application Data

[63] Continuation of Ser. No. 591,944, Mar. 21, 1984, abandoned.

[51] Int. Cl.$^5$ .................. C12N 91/04; C12N 1/20; C12R 1/01
[52] U.S. Cl. .................. 435/260; 435/252.9; 435/267
[58] Field of Search .................. 435/243, 245, 252.9, 435/260, 853, 854, 855, 856, 857, 267

[56] References Cited

U.S. PATENT DOCUMENTS 2,897,600  8/1959  Graham et al. .................. 435/260
2,938,794  5/1960  Herman .................. 435/260

*Primary Examiner*—Elizabeth C. Weimar
*Assistant Examiner*—Irene Marx
*Attorney, Agent, or Firm*—Tilton, Fallon, Lungmus & Chestnut

[57] ABSTRACT

A method is provided for forming stabilized admixtures of dried viable harmless lactic acid producing bacteria. A blend is prepared from a non-toxic particulate carrier and a hydrophilic molecular sieve adsorbent. Preferably the blend contains at least 95% by weight of a carrier which has a very low water absorbing capacity, and the molecular sieve adsorbent is blended in about 0.1 to 2 parts by weight for each 98 to 99.9 parts of the carrier. The resulting admixtures are storable without refrigeration.

9 Claims, No Drawings

STABILIZATION OF DRIED BACTERIA EXTENDED IN PARTICULATE CARRIERS

This is a continuation of application U.S. Ser. No. 519,944, filed Mar. 21, 1984, now abandoned.

FIELD OF INVENTION, BACKGROUND, AND PRIOR ART

The field of this invention relates to the stabilization of dried bacteria against loss of viability during non-refrigerated storage prior to use. More particularly, the invention is concerned with the stabilization of dried bacteria dispersed in particulate carriers.

Living bacteria have heretofore been combined with particulate carriers to provide admixtures which may be stabilized and stored. See, for example, U.S. Pat. Nos. 3,677,898 (Jeffreys), 3,898,132 (Hettrick), and 4,229,544 (Haynes, et al). Jeffreys describes the coating of lactic acid bacteria with an acetylated monoglyceride, and the combining of the coated bacteria with a starch or sugar carrier mixture which may contain minor amounts of inorganic salts. Hettrick mixes bacteria in aqueous dispersions with diatomaceous earth particles to produce a storable dormant mixture. Haynes, et al combines bacteria with a carrier such as peat prior to packaging of the bacteria. Particulate desicants have been proposed for use in the freeze-drying of bacteria, as disclosed in U.S. Pat. Nos. 2,853,797 and 2,897,600, but not for admixture with carrier diluents.

As illustrated by the foregoing patents, the bacteria being stabilized may be intended for a variety of uses in which dilution or extension of a bacterial concentrate is advantageous. The dry bacteria mixtures may be useful in making fermented dairy products, or they may comprise rumen bacteria for feeding to cattle or sheep. They may also be soil bacteria for addition to agricultural soils, or for other purposes.

An important use has developed for *Lactobacillus plantarum* in producing silage. *Lactobacillus acidophilus* is being extensively used with domestic animals to improve their health and well being. In preparing the Lactobacillus for inoculation of silage, and/or for feeding to domestic animals, it is convenient to have the bacteria in highly diluted form, viz. extended in a particulate carrier which is in dry free-flowing condition. But the diluted bacteria must maintain a high degree of stability under non-refrigerated storage conditions for a number of months prior to use. Heretofore the stabilities of lactic acid bacteria in such dispersions have depended on the dry carrier used and the packaging. Results have often been inconsistent with the lactic acid bacteria showing good stability in some dry carriers and poor stability in others. Unpredictable results have been obtained where the same dry carrier that showed good stability at one time later produced poor stability.

No satisfactory method has been known for producing consistent, reproduceable stabilization of bacteria in dry carriers. There is little published scientific data on this subject. From a practical standpoint, the problem has been further complicated by observations that greater instability and greater uncertainty of results occur as the degree of dilution of the bacteria is increased. Yet this is exactly the type of formulation most desired for the large scale uses like those of *L. plantarum* and *acidophilus* referred to above.

Concentrated cultures of lactic acid producing bacteria may be prepared by the method of U.S. Pat. No. 4,115,199. Tripolyphosphate and/or hexametaphosphate are added to the culture medium prior to separation of the cells by centrifugation. The resulting concentrates have usually been frozen with liquid nitrogen for use in manufacturing cheese or other dairy products. However, sufficient stabilization for distribution in a dry non-refrigerated form can be obtained by the method described in U.S. Pat. No. 3,897,307. The cell culture is adjusted to a pH favorable to the stability of the cells on drying, and chemical stabilizers are added comprising an ascorbate compound together with either a glutamate compound or an aspartate compound (viz. ascorbic acid with monosodium glutamate). The bacteria are then dried by a suitable procedure; viz. freeze-drying, spray drying or fluid bed drying. Drying to a low moisture content, such as 2.5 to 3.5% by weight, is desirable. Good stability is obtained when the product is packaged in moisture impervious containers. This permits non-refrigerated storage and distribution for uses such as home manufacture of yogurt. Such stabilization procedures, however, have not been adequate where the bacteria are mixed with relatively large amounts of particulate carriers to form highly extended bacterial admixtures, such as for addition to animal feeds or addition to silage materials.

SUMMARY OF INVENTION

The present invention is concerned with the combination of dried viable bacteria with particulate carriers to form highly diluted admixtures. The degree of dilution of the bacteria on a weight basis is typically from 1:10 to 1:100,000. To achieve non-refrigerated storability of such dilute admixtures, it has been found that the particulate carrier must be selected in relation to its capacity for adsorbing water. The diluting carrier should have a relatively low water adsorbing capacity, such as less than 10% of its moisture free weight when equilibrated in air of 70% relative humidity. Preferably, on the same basis, the water adsorbing capacity of the diluting carrier should be less than one percent. Carriers of this low water adsorbing character are used in admixture with a minor proportion of a hydrophilic molecular sieve adsorbent. The molecular sieve adsorbent is selected to have a high water adsorbing capacity under conditions of low relative humidity. In general, the adsorbent should be capable of adsorbing at least 10% of its moisture free weight when equilibrated in air at 10% relative humidity. In preferred embodiments, the molecular sieve adsorbent is selected so that it will adsorb at least 15% of its moisture free weight when equilibrated in air at 10% relative humidity. Given the conditions specified, a wide variety of particulate carriers can be employed for the dilution of the dry bacteria while achieving storable admixtures that can be packaged in flexible containers, such as laminate-type bags, and distributed and used without refrigeration. The bag laminate should have a low moisture vapor transmission rate (MVTR).

DETAILED DESCRIPTION

A wide variety of particulate carriers may be used in practicing the present invention. The carriers should be in finely divided condition, and should be dry and free-flowing. For most purposes, it is important to employ carriers which are non-toxic, and which can safely be administered to animals or used as ingredients of animal or human foods. A number of common inorganic salts have been found particularly desirable, such as the sodium, potassium or calcium carbonates, bicarbonates, sulfates, and phosphates. Calcium carbonate and sodium sulfate are advantageous for all around use. Such particulate carriers have very low water adsorbing capacity, adsorbing less than 1% of their moisture free weight under high humidity conditions, such as when equilibrated in air of 70% relative humidity However, other carriers of higher water adsorbing capacity can be used. In general, the diluting carrier should adsorb less than 10% of its moisture free weight when equilibrated in air at 70% relative humidity. By-products of the starch, sugar, cheese, and cereal grain industries can be used. For example, providing the water adsorbing capacities referred to above are observed, materials such as whey and soybean meal can be used. Other diluting carriers which may sometimes be employed include various corn cob fractions, wheat midling fractions, corn cones, granulated molasses, and similar edible materials.

The suitability of a diluting carrier for the purpose of this invention can be readily determined by performing moisture equilibration tests. As indicated above, the preferred carriers are those which adsorb less than 1% of their moisture free weight when equilibrated in air at 70% relative humidity, while carriers should be rejected for use if they adsorb more than 10% of their moisture free weight under the same relative humidity condition. A further consideration is the water activity of the carrier in its usual commercial form, as available for use in the present invention. Although the water activity of the carrier may range from 0.10 ($a_w$) up to 0.80 or even higher, such materials can be employed in the present invention without special drying. Where available, however, it is preferred to employ carriers having initial water activities in the range below 0.30, such as 0.10 to 0.25 $a_w$.

The carrier of limited water adsorption capacity, as described above, is used in combination with a minor proportion of a hydrophilic molecular sieve adsorbent. At least 3 parts by weight of the carrier will be employed per part of the adsorbent, that is, 75% by weight or greater of the bacterial admixture will comprise the carrier. In typical embodiments, as little as 5 parts or less of the molecular sieve adsorbent are blended per 95 parts or more of the diluting carrier. The blend will therefore comprise at least 95% by weight of the carrier. In preferred embodiments where the carrier is an inorganic salt, such as those described above, of very low moisture adsorbing capacity, the blend of the carrier with the molecular sieve adsorbent may contain from 98 to 99.9 parts of the carrier together with from 0.1 to 2 parts of the molecular sieve adsorbent.

The adsorbent may be a natural or synthetic zeolite having the capacity to retain water in its molecular pore spaces. Such molecular sieve substances comprise crystalline metal alumino silicates. Commercially available forms are usually alkali metal alumino silicates such as sodium aluminosilicate. These materials are supplied in finely divided condition, and have been activated for water adsorption uses by removal of the water of crystallization during manufacturing. Their content of adsorbed water as supplied commercially is therefore very low. Typical water activities are as low as 0.02 to 0.06 $a_w$. For the purpose of the present invention, the molecular sieve adsorbent should preferably contain substantially no adsorbed water, or at least not over one percent water.

The adsorbent is selected for its high water adsorbing capacity under conditions of low relative humidity. In general, the molecular sieve adsorbent as used in the present invention should have a water adsorbing capacity of at least 10% of its moisture free weight when equilibrated in air at 10% relative humidity. The preferred synthetic zeolites on the same basis have moisture adsorbing capacities of at least 15%. For example, hydrophilic synthetic zeolites can be obtained having moisture adsorbing capacities under conditions of low humidity in the range of 20 to 30% of their moisture free weights. Typical commercial examples are the "Sylosiv" adsorbents sold by the Davison Chemical Division, of W. R. Grace & Co., Baltimore, Md., such as "Sylosiv 120". Similar synthetic zeolite adsorbents are also obtainable from the Linde Division of Union Carbide Corporation, Tarrytown, N.Y. They include "Linde Molecular Sieve 13×", as well as "Linde Molecular Sieve 4A".

The method of this invention can be applied to any dry viable bacteria. After culturing the bacteria according to known procedures, they can be separated from the fermentation media by the method described in U.S. Pat. No. 4,115,199, which in that patent is directed particularly to the recovery of lactic acid producing bacteria. The separation of the media constituents is promoted by adding to the fermentation media from 0.25 to 5.0% based on the weight of the complete culture of tripolyphosphate or a hexametaphosphate containing from 4 to 22 phosphate groups. For example, sodium hexametaphosphate or sodium tripolyphosphate may be used in an amount of 0.5 to 4.0% of the culture. Following addition of the phosphate salt, the cells are recovered by centrifugation in a purified, concentrated form. The cells may then be dried by conventional procedures such as freeze-drying (lyophilization) or spray-drying. Before drying, the pH is preferably adjusted to a pH favoring the stability of the cells, such as a pH from about 6.0 to 6.5. Additives may be incorporated to act as anti-oxidants and/or cryoprotectants. Such additives are disclosed in U.S. Pat. No. 3,897,307. The stabilizers may include a combination of an ascorbate compound selected from L. ascorbic acid and the watersoluble salts thereof, and a second stabilizer selected from the class consisting of glutamic acid, aspartic acid, and the water-soluble salts thereof. For most uses, it is preferred to employ non-toxic or edible additives. The amounts of the additives may comprise use of the ascorbate compound equivalent on a molar basis to 4 to 20 parts by weight of L-ascorbic acid, and the glutamate or aspartate additive in an amount equivalent on a molar basis to 1.5 to 20 parts by weight of monosodium glutamate. Further details of preferred procedures are given in the cited U.S. Pat. No. 3,897,307. This patent relates particularly to the preparation of stabilized dry cultures of lactic acid producing bacteria, but the same procedures can be applied to other bacteria.

Prior to freeze-drying, which is a preferred drying procedure, it is desirable to add one or more cryoprotectants. Such cryoprotectants include substances like inositol, sorbitol, mannitol, glucose, sucrose, etc., as disclosed in greater detail in the cited patent.

A preferred subclass of bacteria for use in the present invention is the harmless lactic acid-producing bacteria. These may be Streptococcus, Lactobacillus, Pediococcus or Leuconostoc species. For example, the Streptococcus species may include:

| *Streptococcus lactis* | *Streptococcus faecium* |

-continued

| | |
|---|---|
| Streptococcus cremoris | Streptococcus faecalis |
| Streptococcus diacetylactis | |
| Streptococcus thermophilus | |

The Lactobacillus may include:

| | |
|---|---|
| Lactobacillus bulgaricus | Lactobacillus coryniformis |
| Lactobacillus acidophilus | subspec. coryniformis |
| Lactobacillus helveticus | Lactobacillus curvatus |
| Lactobacillus bifudus | Lactobacillus brevis |
| Lactobacillus casei | Lactobacillus buchneri |
| Lactobacillus lactis | Lactobacillus fermentum |
| Lactobacillus plantarum | Lactobacillus viridescens |
| Lactobacillus delbrueckii | Lactobacillus amylovorus |
| Lactobacillus thermophilus | Lactobacillus amylophilus |
| Lactobacillus fermetii | Lactobacillus pentosaceus |

The Pediococcus may include:
Pediococcus cerevisiae
Pediococcus acidilactici
Pediococcus pentosaceus
The Leuconostoc species may include:
Leuconostoc cremoris
Leuconostoc dextranicum
Leuconostoc mesenteroides
The invention is also particularly applicable to *Propionibacterium shermanni.*

MANUFACTURING PROCEDURES

In general, the manufacturing operation will comprise the blending of three components: (a) the particulate carrier, (b) the molecular sieve adsorbent, and (c) the dried bacteria. Prior to blending, these ingredients can be maintained in sealed containers in which they are protected from atmospheric humidity. They can therefore be maintained under conditions of low water activity. The freeze-dried bacteria will in general have $a_w$ below 0.10, and the water activity of the activated molecular sieve adsorbent will be very low, such as 0.03 to 0.04 $a_w$. The preferred carriers may also have a relatively low water activity as received, but the method is applicable to particulate carriers over the full range of water activities. It is preferable, however, to select a carrier which under high humidity conditions, such as 70% relative humidity, adsorb less than 10% by their weight of water, and preferably less than 1% of their weight under the same conditions.

In preferred embodiments, only a relatively small proportion of the molecular sieve adsorbent is needed for use with the carrier. For production of a blend having an overall water activity below 0.15, as preferred, such as a water activity in the range of 0.02 to 0.1, a calculation can be made to determine the amount required, depending on the water adsorbing capacity of the molecular sieve adsorbent at the desired final $a_w$. In other words, the total amount of water in the carrier is determined, and then the amount of the molecular sieve adsorbent required to adsorb that amount of water is calculated. The resulting blend will then have a final water activity in the desired range. Some excess of the molecular sieve adsorbent may be included to allow for any water vapor which will penetrate the flexible containers in which the stabilized admixtures are to be stored and distributed. For example, the total surface area of the bag may be determined, and from the moisture vapor transmission rate (MVTR) of the package of material, the amount of moisture which can penetrate under conditions of high humidity, such as 90% R.H. at a standard temperature such as 100° F., can be calculated for a selected storage period, such as 1 year. Even with this excess amount, the amount of the molecular sieve adsorbent in the blend is preferably small, such as 1 to 4% or less.

The blending and packaging operation can be carried out under controlled low humidity conditions, but if this is done with reasonable speed, ordinary atmospheric conditions can be used, such as room temperatures and relative humidities. By carrying out the blending and packaging within periods of 12 to 24 hours, no significant gain in the water activity of the admixture will be produced.

Packaging is preferably in flexible containers, such as laminate-type bags. For example, the bag material may comprise a laminate of paper, aluminum foil, and one or two polyethylene layers. In general, the MVTR of the bag material should be below 0.05, and for optimum results, it should be below 0.005, expressed as $H_2O$ g/100 in$^2$/24 Hr/100° F./90% RH.

The method of this invention is further illustrated by the following specific examples and experimental data.

EXAMPLE I

This example illustrates the preferred mode of practicing this invention, using calcium carbonate as a carrier for *Lactobacillus acidophilus*, and Sylosiv 120 as the molecular sieve adsorbent.

| 1. Ingredients | Initial $a_w$ |
|---|---|
| Lactobacillus acidophilus | 0.04 |
| Calcium carbonate | 0.25 |
| Sylosiv 120 | 0.03 |

The packaging material consists of bags formed from a laminate of Kraft paper (50 lb weight), polyethylene (6 lb weight) aluminum foil (3.5 mils), and low density polyethylene (20 lb. weight). Details of the specifications for packaging are set out below.

| 2. | Packaging | Specifications |
|---|---|---|
| | Dimensions | 17 × 24 in. |
| | MVTR | .002 g/100 in$^2$/24 Hr/ 100° F./90% RH |
| | Storage | 1 year |
| | Package Size | 50 lbs |

| 3. Determining Amount of Sylosiv 120 for Packaging |
|---|
| A. [(17 × 24 in) × (2 sides) × (.002 g)] ÷ 100 in$^2$ = .01632 g H$_2$O vapor penetrated/day |
| B. (.01632 g H$_2$O) × (365 days) = 5.9568 g H$_2$O vapor penetrated/year |
| C. (5.9568 g H$_2$O) ÷ (.20)* = 29.784 g Sylosiv 120 needed/50# bag<br>*Sylosiv 120 adsorbs 20% (.20) H$_2$O ranging from .03–.99 $a_w$. |
| D. (29.784 g) ÷ [(50 lb) × (454 g)] = .001312 |
| E. (.00132) × (2000 lb. batch) = 2.62 lbs. Sylosiv 120 needed to compensate for packaging. |

| 4. Determining Amount of Sylosiv 120 for Calcium Carbonate |
|---|
| [1947.38$^a$ − S) × (.00088$^b$)] ÷ .20$^c$ = 8.53 lbs. Sylosiv 120 needed to lower $a_w$ of calcium carbonate to .03 $a_w$.<br>Where: S is amount of Sylosiv 120<br>$^a$1947.36 lbs [(2000 lbs) − (50 lbs. L.a. + 2.62 lbs. Sylosiv 120)]<br>$^b$Calcium Carbonate at .25 $a_w$ yield .088% (.00088) H$_2$O<br>$^c$Sylosiv 120 adsorbs 20% (.20) H$_2$O |

| 5. Final Formulation | |
|---|---|
| Ingredients | Lbs/Ton |

| -continued | |
|---|---|
| Lactobacillus acidophilus | 50.00 |
| Sylosiv 120 (2.62 + 8.53) | 11.15 |
| Calcium Carbonate | 1938.85 |

6. Manufacturing Instructions

A. 1st Blend molecular sieve adsorbent into particulate carrier. The length of time is dependent on mixer capacity and type. This water activity conditioning is almost immediate.

B. Blend lactic acid bacteria into the conditioned particulate carrier. Again, time is dependent on mixer capacity and type.

C. Following good manufacturing practices fill and package off as soon as possible using heat-sealing type of packaging equipment. For example, a laminate of paper/polyethylene/aluminum foil/low density polyethylene may be used with specifications: 3 ply 50# Kraft paper/6# PE/1.5 mil foil/20# LDPE (Ludlow Packaging, Homer, LA).

EXAMPLE II

This example illustrates the preferred mode of practicing the invention using sodium sulfate as the carrier for *Lactobacillus plantarum*, and Linde 13X molecular sieve adsorbent.

| 1. Ingredients | Initial $a_w$ |
|---|---|
| Lactobacillus plantarum | 0.035 |
| Sodium sulfate | 0.600 |
| Linde 13X | 0.03 |

The specification for the laminate-type packaging material is set out below.

| 2. Packagaing | Specifications |
|---|---|
| Dimensions | 17 × 31 in. |
| MVTR | .0003 g/100 in$^2$/24 hr./ 100° F./90% RH |
| Storage | 1 Year |
| Package Size | 60 lbs. |

3. Determining Amount of Linde 13X for Packaging

A. $[(17 \times 31 \text{ in}) \times (2 \text{ sides}) \times (.0003 \text{ g})] \div 100 \text{ in}^2 =$ .003162 g H$_2$O vapor penetrated/day B. (.003162 g. H$_2$O) × (365 days) = 1.15413 g. H$_2$O vapor penetrated/year C. (1.15413 g. H$_2$O) ÷ (.25)* = 4.61652 g Linde 13X needed/60# bag
 *Linde 13X adsorbs 25% (.25) H$_2$O ranging from .03–.99 $a_w$ D. (4.61652 g) ÷ [(60 lbs) × (454 g)] = .0001694

E. (.0001694) × (2000 lb. batch) = 0.34 lbs. Linde 13X needed to compensate for packaging

4. Determining Amount of Linde 13X for Sodium Sulfate

$[(1959.66^a - L) \times (.00132^b)] \div .25^c = 10.29$ lbs. Linde 13X needed to lower $a_w$ of Sodium Sulfate to .03 $a_w$
Where: L is amount of Linde 13X
$^a$1959.66 lbs. [(2000 lbs) − (40 lbs. L.p. + 0.34 lbs. Linde 13X]
$^b$Sodium Sulfate at .60 $a_w$ yields .132% (.00132) H$_2$O
$^c$Linde 13X adsorbs 25% (.25) H$_2$O

| 5. Final Formulation | |
|---|---|
| Ingredients | Lbs/Ton |
| Lactobacillus plantarum | 40.00 |
| Linde 13X (.34 + 10.29) | 10.63 |
| Sodium Sulfate | 1949.37 |

6. Manufacturing Instructions

The manufacturing and packaging instructions are the same as in Example I, except that the foil layer of the laminate is 3.5 mils to reduce the MVTR.

EXAMPLE III

This example illustrates the use of nonhygroscopic whey as a carrier for a mixture of Lactobacillus and Streptococcus bacteria. The ingredients are set out below.

| 1. Ingredients | Initial $a_w$ |
|---|---|
| Lactobacillus plantarum | 0.035 |
| Lactobacillus acidophilus | 0.04 |
| Streptococcus faecium | 0.06 |
| Streptococcus lactis | 0.05 |
| Nonhygroscopic whey | 0.22 |
| Sylosiv 120 | 0.03 |

The packaging material is the same as that employed in Example I. The packaging specifications are set out below.

| 2. Packaging | Specifications |
|---|---|
| Dimensions | 17 × 24 in. |
| MVTR | .002 g/100 in$^2$/24 Hr/ 100° F./90% RH |
| Storage | 1 year |
| Package Size | 25 lbs. |

3. Determining Amount of Sylosiv 120 for Packaging

A. $[(17 \times 24 \text{ in}) \times (2 \text{ sides}) \times (.002 \text{ g})] \div 100 \text{ in}^2 =$ .01632 g H$_2$O vapor penetrated/day B. (.01632 g H$_2$O) × (365 days) = 5.9568 g H$_2$O vapor penetrated/year C. (5.9568 g H$_2$O) ÷ (.20)* = 29.784 g. Sylosiv 120 needed/25# bag
 *Sylosiv 120 adsorbs 20% (.20) H$_2$O ranging from .03–.99 $a_w$ D. (29.784 g) ÷ [(25 lbs) × (454 g)] = .002641

E. (.0026241) × (2000 lbs. batch) = 5.25 lbs. Sylosiv 120 needed to compensate for packaging.

4. Determining Amount of Sylosiv 120 for Nonhygroscopic Whey

$[(1874.75^a - S) \times (.026)^b] \div .20^c = 215.68$ lbs. Sylosiv 120 needed to lower $a_w$ of nonhygroscopic whey to .03 $a_w$
Where: S is amount of Sylosiv 120
$^a$1874.75 lbs [(2000 lbs) − (120 lbs. Bacteria + 5.25 lbs Sylosiv 120)]
$^b$Nonhygroscopic whey at .22 $a_w$ yields 2.6% (.026) H$_2$O
$^c$Sylosiv 120 adsorbs 20% (.20) H$_2$O

| 5. Final Formulation | |
|---|---|
| Ingredients | Lbs/Ton |
| Lactobacillus plantarum | 50.00 |
| Lactobacillus acidophilus | 35.00 |
| Streptococcus faecium | 25.00 |
| Streptococcus lactis | 10.00 |
| Sylosiv 120 (5.25 + 215.68) | 220.93 |
| Nonhygroscopic Whey | 1659.07 |

6. Manufacturing Instructions

The manufacturing and packaging instructions are the same as in Example I.

EXAMPLE IV

This example illustrated the use of corn cob granules as the carrier for *Lactobacillus acidophilus*. The ingredients are set out below.

| 1. Ingredients | Initial $a_w$ |
|---|---|
| Lactobacillus acidophilus | 0.04 |
| Corn Cob Granules | 0.60 |
| Linde 13X | 0.03 |

The packaging laminate is the same as that used in Example II. The packaging specifications are as follows.

| 2. | Packaging | Specifications |
|---|---|---|
| | Dimensions | 17 × 31 in. |
| | MVTR | .0003 g/100 in$^2$/24 Hr/ 100° F./90% RH |
| | Storage | 1 year |
| | Package Size | 20 Lbs. |

3. Determining Amount of Linde 13X for Packaging

A. [(17 × 31 in) × (2 sides) × (.0003 g)] ÷ 100 in$^2$ = .003162 g H$_2$O vapor penetrated/day
B. (.003162 g H$_2$O) ÷ (.25)* = 4.61652 g. H$_2$O vapor penetrated/year
C. (1.15413 g H$_2$O) → (.25)* = 4.61652 g. Linde 13X needed/20# bag
  *Linde 13X adsorbs 25% (.25) H$_2$O ranging from .03–.99 $a_w$
D. (4.61652 g) ÷ [(20 lbs) × (454 g)] = .0005084
E. (.0005084) × (2000 lb. batch) = 1.02 lbs. Linde 13X needed to compensate for packaging.

4. Determining Amount of Linde 13X for Corn Cob Granules

[(1923.98$^a$ − L) × (.09)$^b$] ÷ .25$^c$ = 509.29 lb. Linde 13X needed to lower $a_w$ of corn cob granules to .03 $a_w$
Where: L is amount of Linde 13X
$^a$1923.98 lbs. [(2000 lbs) − (75 lbs. L.a. + 1.02 lbs. Linde 13X)]
$^b$Corn cob granules at .60 $a_w$ yields 9.0% (.09) H$_2$O
$^c$Linde 13X adsorbs 25% (.25) H$_2$O

5. Final Formulation

| Ingredients | Lbs/Ton |
|---|---|
| Lactobacillus acidophilus | 75.00 |
| Linde 13X (1.02 + 509.29) | 510.31 |
| Corn Cob Granules | 1414.69 |

6. Manufacturing Instructions

The manufacturing and packaging instructions are the same as in Example II.

EXAMPLE V

This example presents the results of experiments demonstrating the value of the present invention in stabilizing dry bacteria extended in particulate carriers. The details of the test procedure are summarized below.

1. Particulate Carriers and Conditioning

A. Carriers were chosen which have been typically used as carriers for agricultural-related products.
B. Carrier samples were split (from same lot) conditioning one-half with molecular sieve adsorbant. The other half was not subjected to any conditioning (control).
C. Sylosiv 120 was added in calculated amounts required to achieve the initial $a_w$ values shown in the tables, the calculations being as illustrated in Examples I to IV.

2. Bacterial Additions

Dried lactic acid bacteria (i.e. *L. acidophilus* and *L. plantarum*) were equally added to the control carrier and conditioned carrier. The bacteria had been concentrated and stabilized as described in U.S. Pat. Nos. 4,115,199 and 3,897,307.

3. Blending/Packaging

After thorough blending, 60 gm. of sample were placed in moisture-proof pouches yielding approximately 10–12 pouches for control + 10–12 pouches for conditioned.

4. Testing

After each designated time interval, a pouch from each group was opened, water activities and microbiological platings were run. All pouches were stored at ambient temperature (23° C.). For *L. acidophilus* platings, MRS agar was used and for *L. plantarum* platings, LBS agar was used.

5. Results

The results are summarized in Tables A and B. In all cases, the stability of the bacteria were statistically improved when the water activity was lowered and controlled by addition of the molecular sieve adsorbent, regardless of the type of carrier used and degree of dilution with the bacteria.

TABLE A

*LACTOBACILLUS ACIDOPHILUS* VS. CARRIERS @ 23° C. STORAGE

| DAYS | CALCIUM CARBONATE CONTROL | CALCIUM CARBONATE CONDITIONED | CORN COB FRACTIONS CONTROL | CORN COB FRACTIONS CONDITIONED | SODIUM BICARBONATE CONTROL | SODIUM BICARBONATE CONITIONED | NONHYGROSCOPIC WHEY CONTROL | NONHYGROSCOPIC WHEY CONDITIONED |
|---|---|---|---|---|---|---|---|---|
| 0 | 83 × 10$^6$ | 18 × 10$^7$ | 51 × 10$^7$ | 17 × 10$^8$ | 26 × 10$^7$ | 25 × 10$^7$ | 21 × 10$^7$ | 32 × 10$^7$ |
| 30 | 35 × 10$^6$ | 15 × 10$^7$ | 20 × 10$^2$ | 10 × 10$^8$ | 18 × 10$^7$ | 25 × 10$^7$ | 57 × 10$^6$ | 20 × 10$^7$ |
| 60 | 10 × 10$^5$ | 62 × 10$^6$ | Discontinued | 33 × 10$^7$ | 85 × 10$^6$ | 19 × 10$^7$ | 18 × 10$^6$ | 14 × 10$^7$ |
| 90 | 16 × 10$^5$ | 24 × 10$^6$ | Discontinued | 18 × 10$^7$ | 44 × 10$^6$ | 20 × 10$^7$ | 16 × 10$^6$ | 12 × 10$^7$ |
| 120 | 11 × 10$^5$ | 20 × 10$^6$ | Discontinued | 14 × 10$^7$ | 23 × 10$^6$ | 21 × 10$^7$ | 83 × 10$^5$ | 10 × 10$^7$ |
| 150 | 27 × 10$^3$ | 15 × 10$^6$ | Discontinued | 17 × 10$^7$ | 31 × 10$^5$ | 15 × 10$^7$ | 66 × 10$^5$ | 88 × 10$^6$ |
| 180 | 75 × 10$^2$ | 70 × 10$^5$ | Discontinued | NA | NA | NA | 23 × 10$^5$ | 35 × 10$^6$ |
| $a_w$ | .29 vs. .07 | | .61 vs. .19 | | .26 vs. .08 | | .21 vs. .06 | |

(1) All values expressed as CFU/gm of total mixtures.
(2) NA — Not available.
(3) In order to eliminate any variations in water activity samples were placed in moisture-resistant paper/foil/poly pouches.
(4) The bacterial concentration in the mixtures was in the range of 0.15 to 0.30 wt. %.

TABLE B

| | LACTOBACILLUS PLATARUM VS. CARRIERS @ 23° C. STORAGE | | | | | |
| --- | --- | --- | --- | --- | --- | --- |
| | CALCIUM CARBONATE | | NONHYGROSCOPIC WHEY | | SODIUM SULFATE | |
| DAYS | CONTROL | CONDITIONED | CONTROL | CONDITIONED | CONTROL | CONDITIONED |
| 0 | $43 \times 10^8$ | $45 \times 10^8$ | $58 \times 10^8$ | $59 \times 10^8$ | $14 \times 10^7$ | $39 \times 10^7$ |
| 30 | $28 \times 10^8$ | $48 \times 10^8$ | $32 \times 10^8$ | $33 \times 10^8$ | $81 \times 10^5$ | $38 \times 10^7$ |
| 60 | $33 \times 10^8$ | $55 \times 10^8$ | $15 \times 10^8$ | $55 \times 10^8$ | $69 \times 10^5$ | $49 \times 10^7$ |
| 90 | $16 \times 10^7$ | $28 \times 10^8$ | $56 \times 10^7$ | $40 \times 10^8$ | NA | NA |
| 120 | $77 \times 10^6$ | $35 \times 10^8$ | $35 \times 10^7$ | $52 \times 10^8$ | NA | NA |
| 150 | $42 \times 10^4$ | $20 \times 10^8$ | $36 \times 10^7$ | $48 \times 10^8$ | NA | NA |
| 180 | NA | NA | $28 \times 10^7$ | $51 \times 10^8$ | NA | NA |
| $a_w$ | .31 vs. .09 | | .21 vs. .07 | | .29 vs. .03 | |

(1) All values expressed as CFU/gm of total mixtures.
(2) NA — Not available.
(3) In order to eliminate any variations in water activity samples were placed in moisture-resistant paper/foil/poly pouches.
(4) The bacterial concentration in the mixtures was in the range of 0.15 to 0.25 wt. %.

We claim:
1. The method of forming stabilized admixtures of dried viable harmless lactic acid producing bacteria, comprising:
   (a) preparing a blend by intermixing a non-toxic particulate carrier with a hydrophilic molecular sieve absorbent, said blend containing at least about 95% by weight of said carrier which carrier has a water absorbing capacity of less than one percent of its moisture free weight when equilibrated in air of 70% relative humidity, said molecular sieve absorbent having a water absorbing capacity of at least 15% of its moisture free weight when equilibrated in air at 10% relative humidity and being blended in 0.1 to 2 parts by weight per each 98 to 99.9 parts of said carrier; and
   (b) dispersing in said blend either during the intermixing of step (a) or subsequent thereto said lactic acid product bacteria to form a highly diluted admixture thereof which is storable without refrigeration.
2. The method of claim 1 in which said molecular sieve adsorbent is a synthetic zeolite.
3. The method of claim 1 in which said carrier is an inorganic salt administrable to animals selected from the class consisting of sodium and calcium carbonates, bicarbonates, sulfates, or phosphates.
4. The method of claim 1 in which said bacteria is *Lactobacillus acidophilus*.
5. The method of claim 1 in which said bacteria is *Lactobacillus plantarum*.
6. The method of forming stabilized admixtures of dried viable harmless lactic acid producing bacteria highly extended in a particulate carrier, comprising:
   (a) preparing a blend by intermixing from 98 to 99.9 parts by weight of a non-toxic particulate carrier with from 0.1 to 2 parts by weight of a hydrophilic molecular sieve synthetic zeolite adsorbent, said carrier having a water adsorbing capacity of less than one percent of its moisture free weight when equilibrated in air at 70% relative humidity, said zeolite adsorbent having a water adsorbing capacity of at least 15% of its moisture free weight when equilibrated in air at 10% relative humidity; and
   (b) dispersing in said blend either during the intermixing of step (a) or subsequent thereto said lactic acid producing bacteria to form a highly diluted storable admixture thereof.
7. The method of claim 6 in which said stabilized admixtures contain said viable bacteria in amounts of from about $5 \times 10^{10}$ to $1 \times 10^6$ CFU per gram of said blend.
8. The method of claim 6 in which said bacteria is *Lactobacillus acidophilus*.
9. The method of claim 6 in which said bacteria is *Lactobacillus plantarum*.

* * * * *